United States Patent [19]

Muramatsu et al.

[11] 4,342,677

[45] Aug. 3, 1982

[54] FLUOROCOMPLEX SALT-CONTAINING LIQUID FOR SETTING DENTAL CEMENTS

[75] Inventors: Hiroaki Muramatsu, Gotenba; Kentaro Tomioka, Chofu; Kazuo Hirota, Tokyo; Shoji Akahane, both of Tokyo, all of Japan

[73] Assignee: G-C Dental Industrial Corp., Tokyo, Japan

[21] Appl. No.: 263,589

[22] Filed: May 14, 1981

[30] Foreign Application Priority Data

Jun. 4, 1980 [JP] Japan .................................. 55-74408

[51] Int. Cl.[3] .............................................. C08K 3/30

[52] U.S. Cl. ..................................... 523/116; 524/559

[58] Field of Search ..................... 260/29.6 M, 29.6 H

[56] References Cited

U.S. PATENT DOCUMENTS

| | | | |
|---|---|---|---|
| 3,655,605 | 4/1972 | Smith | 260/29.6 M |
| 3,741,926 | 6/1973 | Jurecic | 260/29.6 M |
| 3,751,391 | 8/1973 | Smith | 260/29.6 M |
| 3,986,998 | 10/1976 | Schmitt et al. | 260/29.6 WB |
| 4,016,124 | 4/1977 | Crisp et al. | 260/29.6 M |
| 4,082,722 | 4/1978 | Schmitt et al. | 260/42.43 |
| 4,209,434 | 6/1980 | Wilson et al. | 260/29.6 H |
| 4,222,920 | 9/1980 | Crisp et al. | 260/29.6 M |
| 4,271,057 | 6/1981 | Drake et al. | 260/29.6 M |
| 4,288,355 | 9/1981 | Anderson et al. | 260/29.6 M |

*Primary Examiner*—Joseph L. Schofer
*Assistant Examiner*—Bernard Lipman
*Attorney, Agent, or Firm*—Oblon, Fisher, Spivak, McClelland & Maier

[57] ABSTRACT

A liquid for setting dental cements comprising a aqueous solution of a copolymer of acryclic acid and maleic acid, tartaric acid and one or more fluorocomplex salt.

5 Claims, No Drawings

FLUOROCOMPLEX SALT-CONTAINING LIQUID FOR SETTING DENTAL CEMENTS

BACKGROUND OF THE INVENTION

The present invention is generally concerned with improvements in or relating to dental cements, among others, glass ionomer cements. In particular, it pertains to a novel liquid for setting dental cements which excels markedly in crushing strength, water resisting property and manipulation characteristics during mixing.

The glass ionomer cements that have main use in dentistry are prepared by setting fluoroaluminosilicate glass and a polycarboxyic acid such as polyacrylic acid under the presence of water, and their appearance is good thanks to the transparency of the glass mixed-in. In particular, the cements of this type have little or no detrimental corrosive or other harmful pathological action upon the pulp, exhibit satisfactory adhesion to both teeth, dentin and enamel, excel in marginal sealing property and maintain their resistance to the mouth tissues or fluids over an extended period of time. Owing to their unique capabilities, from which is free the commerically available composite resin of the resin type, the glass ionomer cements find important use as restorations, for anterior teeth and as binders for prostheses, other linings or building-up. However, the glass ionomer cements which comprises a mere combination of an aqueous solution of polyacrylic acid and powders of fluoroaluminosilicate glass have now been found to be disadvantageous in that they provided a mixed product which is inferior in fluidity and manipulation characteristics, and takes a longer period of time for setting. As a result, the mixed product comes at its surface into contact with the oral fluids and disintegrates to such an extent that it becomes brittle, thus resulting in a lowering of the final strength. Laid-open Japanese Patent Application No. 101893/1977 specification discloses a process that does not offer such problems, and yet has advantages over the prior art. According to this process, 7 to 25% by weight of one or two or more of polybasic carboxylic acids are added to a 45 to 60% by weight aqueous solution of polyacrylic acid to prepare a setting liquid. In fact, this liquid is easy manipulate so that setting is complete within a short period of time, and gives rise to increases in strength. When used as fillings for oral restorations, however, the setting liquid as referred to above is susceptible to the mouth fluids and humidity, and has a cloudy tendency. For this reason, it is ordinarily required to apply a waterproofing treatment which comprises coating a waterproof varnish on the surface of the mixed product followed by sufficient drying, to thereby form a waterproof film. These procedures are tolerably troublesome and time-consuming as compared with the manipulation for filling the composite resin for the dental restoration.

DETAILED DESCRIPTION OF THE INVENTION AND PREFERRED EMBODIMENTS

As a consequence of extensive and intensive studies made concerning the polymer acid components and the additives with the intension of providing a solution to the above-mentioned problems, it has now surprisingly been found that a novel glass ionomer cement, which excels markedly in strength, enables a setting reaction to proceed rapidly, and is superior in water resisting property, is obtained by using a copolymer of acrylic acid and maleic acid, that is now proved to be best suited for use as the polymer acid in a setting liquid, and adding thereto tartaric acid and a specific fluorine compound.

More specifically, the present invention provides a liquid for setting dental cements, in which a 45 to 55% by weight aqueous solution of a copolymer of acrylic acid and maleic acid contains tartaric acid and one or more of fluorocomplex salts in amounts of 10–25% by weight and 0.1–5% by weight based on the total weight, respectively.

As the powdery for dental cement used in combination with the setting liquid according to the present invention, preference is given to the powders formulated by pulverization of the so-called fluoroaluminosilicate glass prepared by blending together 37 to 45% by weight of silicic anhydride, 25 to 35% by weight of aluminium oxide, 5 to 13% by weight of calcium oxide, 10 to 15% by weight of soda fluoride and 3 to 7% by weight of calcium phosphate and firing the resultant blend at about 1300° C. In analogy with a dental silicophosphate cement powder, however, no difficulty will be encountered in mixing the above-mentioned powders with the powders for a zinc phosphate cement obtained by firing of blending ingredients consisting mainly of 90 parts by weight of zinc oxide and 10 parts by weight of magnesium oxide. According to the present invention, a copolymer of acrylic acid, particularly of acrylic and maleic acid, is preferably used as the polymer acid. Preferably, the acrylic acid amounts to 60% or more in the copolymer.

The copolymer of acrylic acid and maleic acid according to the present invention has preferably a mean molecular weight of no more than 30,000, particularly 20,000 to 5,000. The molecular weight may be adjusted by selection of a polymerization regulator having a proper chain transfer constant, such as isopropyl alcohol, dodecyl mercaptane, thioglycolic acid, etc.

The term "mean molecular weight" used herein shall be determined on the basis of viscosity measurement according to the following calculating procedures: An intrinsic viscosity $[\eta]$ is measured in a 2 N aqueous solution of caustic soda at 25° C., and an average molecular weight M is computed from the Sakamoto.s empirical equation.

$$[\eta]=1.21\times10^{-3}\times M^{0.54}\ (100\ \text{ml/g},\ 25°\ \text{C.})$$

(This equation is cited from a publication The Journal of the Chemical Society of Japan 83 386 (1962).

In the present invention, the tartaric acid is preferably used in proportions of 10 to 25%, particularly 10 to 15%, on the basis of the total weight.

The fluorocomplex salts effectively used in the present invention include, for instance, potassium tetrafluoroberyllate, ammonium tetrafluoroberylliumate, sodium hexafluorozirconate, potassium hexafluorozirconate, potassium heptafluoroniobate, potassium heptafluorotantalate, sodium hexafluorosilicate, potassium hexafluorosilicate, litium hexafluorosilicate, ammonium hexafluorosilicate, iron hexafluorosilicate, nickel hexafluorosilicate, zinc hexafluorosilicate, tin hexafluorosilicate, magnesium hexafluorosilicate, manganese hexafluorosilicate, sodium hexafluorotitanate, potassium hexafluorotitanate, ammonium hexafluorotitanate, nickel hexafluorotitanate, potassium tetrafluoroborate, ammonium tetrafluoroborate, manganese tetrafluoroborate, iron tetrafluoroborate, nickel tetrafluoroborate, tin tetrafluoroborate, indium tetrafluoroborate, zinc tetrafluoroborate, antimony tetrafluoroborate, boron trifluoride-acetate complex an so on. Most preferably are potassium tetrafluoroberyllate, sodium hexafluorozirconate, potassium hexafluorozirconate, sodium hexafluorosilicate, potassium hexafluorosilicate, zinc hexafluorosilicate, magnesium hexafluorosilicate, sodium hexafluorotitanate, potassium hexafluorotitanate and ammonium hexafluorotitanate.

These complex salts have a marked effect even in small quantities, but the amount of dissolution thereof in a polymer solution is generally limited owing to their less solubility. In addition, they exert a slight effect on increases in strength, even if they are added in larger amounts. For this reason, the amounts of the fluorocomplex salts added to the copolymer of acrylic acid and maleic acid range from 0.1 to 5% by weight, more preferably 0.1 to 3% by weight.

In principle, the fluorocomplex salts should be added directly to a copolymer solution. Due to their less solubility, however, there is a possibility that they may be dispersed in and mixed with dental cement powders composed mainly of the fluoroaluminosilicate glass, if necessary. The fluorocomplex salt powders added to the dental cement powders should have been finely divided such that they can pass through a 400-mesh sieve. 0.1 to 10% by weight, preferably 0.1 to 6% by weight of such powders is then added to and dispersed in the cement powders under mixing. The obtained product is mixed with the setting liquid, the composition of which is defined in the appended claims and which may or may not contain the fluorocomplex salts, to thereby form a mixed product which may be used as a dental cement.

Likewise, the copolymer of acrylic acid and maleic acid and the tartaric acid may wholly or partly be applied in the powdery form.

The glass ionomer cement uses the fluoroaluminosilicate glass as the powdery ingredient, and it is proved that considerable amount of fluorine passes into the dentin in an earlier stage when the cement mud obtained by mixing and blending the cement with a solution of the copolymer of acrylic acid and maleic acid is brought into contact with the dentate tissues, thus preventing effectively the initial corrosion thereof. The addition of the fluorocomplex salts enhances further such a preventing effect.

The present invention will now be elucidated with reference to the following examples and controls.

Examples 1-4 and Controls 1-3

In an ordinal container (flask or beaker), given quantities of tartaric acid and fluorocomplex salts were added to an aqueous solution of a copolymer of acrylic acid and maleic acid having a predetermined concentration. The container was sufficiently shaked, plugged and allowed to stand for 3 to 5 days in a thermostatic chamber, to thereby prepare a colorless and transparent solution. In this way, four types of the setting liquid according to the present invention were formulated.

In controls, three types of the setting liquids the composition of which is specified in Table 1, were prepared in a similar way.

In the table, the bracketed figures refer to the average molecular weight of the acrylic-maleic acid copolymers used, which was determined according to the foregoing procedures.

1.0 gram of each of the setting liquids thus formulated was blended with 1.4 grams of a dental cement powder specified below for about 30 seconds. The resultant blend was then measured on setting time, ad crushing strength and solubility after the lapse of 24 hours in accordance with the procedures provided by JIS T6602.

Dental Cement Powder: manufactured by G.C. Dental Industrial Corp., and sold under the trade name of NEW LUSILEX.

This powder is formulated by heat treatment of starting materials consisting of 40% by weight of silica sand, 26% by weight of alumina, 12% by weight soda fluoride, 15% by weight of lime carbonate and 7% by weight of lime phosphate at about 1300° C.

The results are set forth in Table 2 which also shows JIS T6602 standard concerning zinc phosphate cement.

TABLE 1

| Ex. No. | Composition of Setting Liquid | |
|---|---|---|
| 1 | Copolymer of 95% acrylic acid and 5% maleic acid (7500) | 45.0 |
| | Pure water | 44.8 |
| | Tartaric acid | 10.0 |
| | Potassium hexafluorosilicate | 0.2 |
| 2 | Copolymer of 90% acrylic acid and 10% maleic acid (5800) | 45.0 |
| | Pure water | 38.0 |
| | Tartaric acid | 15.0 |
| | Sodium hexafluorotitanate | 2.0 |
| 3 | Copolymer of 80% acrylic acid and 20% maleic acid (15200) | 43.5 |
| | Pure water | 44.0 |
| | Tartaric acid | 10.0 |
| | Potassium hexafluorozirconate | 2.5 |
| 4 | Copolymer of 90% acrylic acid and 10% maleic acid (7500) | 39.0 |
| | Pure water | 44.0 |
| | Tartaric acid | 14.0 |
| | Sodium hexafluorotitanate | 1.0 |
| | Potassium hexafluorozirconate | 2.0 |
| Control 1 | Copolymer of 90% acrylic acid and 10% maleic acid (5800) | 50.0 |
| | Pure water | 50.0 |
| Control 2 | Copolymer of 90% acrylic acid and 10% maleic acid (7500) | 47.0 |
| | Pure water | 50.0 |
| | Tartaric acid | 3.0 |

TABLE 2

| Ex. No. | Setting time in minutes | Crushing Strength in $Kg/cm^2$ | Solubility in % |
|---|---|---|---|
| 1 | 6.0 | 1520 | 0.6 |
| 2 | 5.0 | 1710 | 0.5 |
| 3 | 4.5 | 1660 | 0.4 |
| 4 | 5.0 | 1720 | 0.4 |
| Control 1 | 12.0 | 820 | 1.0 |
| Control 2 | 10.5 | 1010 | 0.8 |
| JIS T6602 Standard | 4 ~ 8 | 700 or above | 0.2% or below |

The results as tabulated above indicate that the setting liquid of the present invention has a setting time ranging from 5 to 6 minutes which is most effective from the clinical viewpoint, and a crushing strength higher than the JIS standard by a factor of two or more.

While it is generally said that the glass ionomer cement possesses a solubility far greater than that of the zinc phosphate cement, the setting liquid of the present invention has turned out to give rise to considerable increases in solubility.

From a comparison with the Control 2 in which the copolymer solution contains tartaric acid alone, it is also found that the fluorocomplex salts have a marked effect.

1.0 gram of the setting liquid obtained in Example 1 or 4 was blended with 2.2 grams of the aforesaid dental cement for 30 seconds. The resultant product was then measured on setting time, crushing strength after 24 hours, and solubility after the lapse of 7 days according to the procedures provided in JIS T6603. The results are given in Table 3 which also shows the test results of a silicate cement (W Corp.) (Control 3) and the JIS T6603 standard concerning it.

TABLE 3

| Ex. No. | Setting Time in minutes | Crushing Strength in Kg/cm$^2$ | Solubility in % |
|---|---|---|---|
| 6 | 4.0 | 2110 | 0.3 |
| 7 | 3.5 | 2260 | 0.2 |
| Control 3 | 3.5 | 1890 | 0.9 |
| JIS T6603 Standard | 3 ~ 8 | 1500 or above | 1.5% or below |

The results show that the crushing strength increases with the amount of the cement. A comparison of the examples and the control also indicates that the setting liquid of the present invention is superior in the manipulation characteristics due to its less solubility, and is most effective for the filling purpose.

What is claimed as new and desired to be secured by Letters Patent of the United States is:

1. A liquid for setting dental cements comprising an aqueous solution of 45 to 55% by weight of a copolymer of acrylic acid and maleic acid containing tartaric acid and one or more fluorocomplex salts in amounts of 0.1 to 5% on the basis of the total weight.

2. A liquid for setting dental cements as recited in claim 1, in which the fluorocomplex salt used is selected from the group consisting of potassium tetrafluoroberyllate, ammonium tetrafluoroberyllate, sodium hexafluorozirconate, potassium hexafluorozirconate, potassium heptafluoroniobate, potassium heptafluorotantalate, sodium hexafluorosilicate, potassium hexafluorosilicate, lithium hexafluorosilicate, ammonium hexafluorosilicate, iron hexafluorosilicate, nickel hexafluorosilicate, zinc hexafluorosilicate, tin hexafluorosilicate, magnesium hexafluorosilicate, sodium hexafluorotitanate, potassium hexafluorotitanate, ammonium hexafluorotitanate, nickel hexafluorotitanate, potassium tetrafluoroborate, ammonium tetrafluoroborate, manganese tetrafluoroborate, iron tetrafluoroborate, nickel tetrafluoroborate, tin tetrafluoroborate, indium tetrafluoroborate, zinc tetrafluoroborate, antimony tetrafluoroborate, and boron trifluoride-acetate complex.

3. A liquid for setting dental cements as recited in claim 2, in which the fluorocomplex salts used is selected from the group consisting of potassium tetrafluoroberyllate, sodium hexafluorozirconate, potassium hexafluorozirconate, zinc hexafluorosilicate, magnesium hexafluorosilicate, sodium hexafluorotitanate, potassium hexafluorotitanate and ammonium hexafluorotitanate.

4. A liquid for setting dental cement according to claim 1, containing 10 to 25% by weight of tartaric acid.

5. A liquid for setting dental cements as recited in claim 1, in which the copolymer of acrylic acid and maleic acid has an average molecular weight of no more than 30,000, preferably 20,000 to 5,000 as calculated from the following equation:

$$[\eta]=1.2\times10^{-3}\times M^{0.54}\ (100\ ml/g,\ 25^\circ)$$

wherein $[\eta]$ stands for an intrinsic viscosity; and M denotes an average molecular weight.

* * * * *